United States Patent

Nosco et al.

[11] Patent Number: 5,520,904
[45] Date of Patent: May 28, 1996

[54] CALCIUM/OXYANION-CONTAINING PARTICLES WITH A POLYMERICAL ALKOXY COATING FOR USE IN MEDICAL DIAGNOSTIC IMAGING

[75] Inventors: Dennis L. Nosco, Florissant; Sandeep Nema; Alexander L. Klibanov, both of St. Louis; Kofi Adzamli, Chesterfield, all of Mo.

[73] Assignee: Mallinckrodt Medical, Inc., St. Louis, Mo.

[21] Appl. No.: 379,063

[22] Filed: Jan. 27, 1995

[51] Int. Cl.$^6$ ............................ A61B 5/055; A61K 49/04
[52] U.S. Cl. ........................ 424/9.322; 424/9.323; 424/9.411; 424/9.47; 436/173
[58] Field of Search ......................... 424/9.322, 9.323, 424/9.411, 9.42; 436/173; 128/653.4, 654; 423/263, 301, 305

[56] References Cited

U.S. PATENT DOCUMENTS

| | | | |
|---|---|---|---|
| 4,079,124 | 3/1978 | Winchell | 424/4 |
| 4,185,225 | 8/1989 | Wahlig et al. | 424/423 |
| 4,243,652 | 1/1981 | Francis | 424/1 |
| 4,657,755 | 4/1987 | Christensen et al. | 424/1.1 |
| 4,680,171 | 7/1987 | Shell | 424/5 |
| 4,709,703 | 12/1987 | Lazarow et al. | 128/654 |
| 4,880,007 | 11/1989 | Sadler et al. | 128/653 |
| 4,888,248 | 12/1989 | Hirai et al. | 438/403 |
| 5,009,898 | 4/1991 | Sakuma et al. | 424/618 |
| 5,047,031 | 9/1991 | Constantz | 606/77 |
| 5,055,307 | 10/1991 | Tsuru et al. | 424/493 |
| 5,122,363 | 6/1992 | Balkus, Jr. et al. | 424/9 |
| 5,160,725 | 11/1992 | Pilgrimm | 424/9 |
| 5,186,922 | 2/1993 | Shell et al. | 128/654 |
| 5,225,282 | 7/1993 | Chagnon et al. | 428/407 |
| 5,330,742 | 7/1994 | Deutsch et al. | 424/9 |
| 5,342,609 | 8/1994 | Meeh et al. | 424/9 |
| 5,407,659 | 4/1995 | Deutsch et al. | 424/9 |
| 5,429,814 | 7/1995 | Young et al. | 424/9.31 |

FOREIGN PATENT DOCUMENTS

| | | | |
|---|---|---|---|
| 0210043 | 1/1987 | European Pat. Off. | A61K 49/04 |
| 0343934 | 11/1989 | European Pat. Off. | H01F 1/36 |
| 0361797 | 4/1990 | European Pat. Off. | C03C 10/00 |
| 0499299 | 8/1992 | European Pat. Off. | A61K 47/48 |

*Primary Examiner*—Gary E. Hollinden
*Attorney, Agent, or Firm*—Brian K. Stierwalt

[57] ABSTRACT

The present invention provides new and structurally diverse particulates for use in magnetic resonance imaging and X-ray contrast imaging of body organs and tissues having the following general formula:

$$Ca_n M_m X_r Y_s$$

wherein M is a paramagnetic ion or stoichiometric mixture of metal ions having a valence of 2+ or 3+; X is a simple anion; Y is a tetrahedral oxyanion, or mixtures thereof; m is an integer greater than or equal to 1; n is an integer greater than or equal to 1; r and s are integers and are adjusted as needed to provide charge neutrality; and further comprising a polyalkoxy compound.

Methods for using and making particles of the invention are also disclosed.

52 Claims, No Drawings

CALCIUM/OXYANION-CONTAINING PARTICLES WITH A POLYMERICAL ALKOXY COATING FOR USE IN MEDICAL DIAGNOSTIC IMAGING

FIELD OF THE INVENTION

The invention is in the field of imaging. In particular the invention relates to calcium/oxyanion-containing particles for use in medical diagnostic imaging, such as magnetic resonance imaging ("MRI") and X-ray.

BACKGROUND OF THE INVENTION

The use of contrast agents in diagnostic medicine is rapidly growing. In X-ray diagnostics, for example, increased contrast of internal organs, such as the kidneys, the urinary tract, the digestive tract, the vascular system of the heart (angiography), and so forth, is obtained by administering a contrast agent which is substantially radiopaque. In conventional proton MRI diagnostics, increased contrast of internal organs and tissues may be obtained by administering compositions containing paramagnetic metal species which increase the relaxivity of surrounding protons.

Often it is desirable to image or treat a specific organ or tissue. Effective organ or tissue-specific diagnostic agents accumulate in the organ or tissue of interest. Copending patent application Ser. No. 07/948,540, filed Sep. 22, 1992, titled "Treated Apatite Particles for Medical Diagnostic Imaging," which is incorporated herein by reference, discloses the preparation and use of apatite particles for medical diagnostic imaging. This patent application also describes methods for preparing apatite particles which provide organ or tissue-specific contrast. By carefully controlling the particle size and route of administration, organ specific imaging of the liver, spleen, gastrointestinal tract, or blood pool is obtained.

A need continues to exist for new and structurally diverse compounds for use as imaging agents. There is a further need to develop highly stable compounds with good relaxivity characteristics that show improved specificity for particular organs and tissues.

SUMMARY OF THE INVENTION

The present invention provides new and structurally diverse particulates for use in magnetic resonance imaging and X-ray contrast imaging of body organs and tissues having the following general formula:

$$Ca_n M_m X_r Y_s$$

wherein M is a paramagnetic ion or stoichiometric mixture of metal ions having a valence of 2+ or 3+; X is a simple anion; Y is a tetrahedral oxyanion, or mixtures thereof; m is an integer greater than or equal to 1; n is an integer greater than or equal to 1; r and s are integers and are adjusted as needed to provide charge neutrality; and further comprising a polyalkoxy compound.

Methods for using particles and agents of the invention and methods for making agents of the invention are also disclosed.

As used in this document, "calcium/oxyanion-containing particles" refers to the above defined formula, "coating" refers to the polymers comprising a polyalkoxy compound attached to the calcium/oxyanion containing particles, and "agent" generally refers to the coated particle.

DETAILED DESCRIPTION OF THE INVENTION

Calcium/oxyanion particles are prepared by modifying conventional methods for preparing hydroxyapatite (sometimes referred to as "hydroxylapatite"). For example, stoichiometric hydroxyapatite, $Ca_{10}(OH)_2(PO_4)_6$, can be prepared by adding an ammonium phosphate solution to a solution of calcium/ammonium hydroxide. Useful apatite particles may also be prepared by replacing calcium with paramagnetic metal ions. Other apatite derivatives are prepared by replacing the $OH^-$ with simple anions, including $F^-$, $Br^-$, $I^-$, or $½[CO_3^{2-}]$ and by replacing calciums with other alkali or alkaline earth metals. Various techniques for controlling the particle size for certain calcium phosphate-containing compounds (apatites) are disclosed in copending application Ser. No. 07/948,540. For example, slower addition rates (introduction of the precipitating anion or cation), faster stirring, higher reaction temperatures, and lower concentrations can result in smaller particles. In addition, sonication during precipitation, turbulent flow or impingement mixers, homogenization, and pH modification may be used to control particle size. Other means, such as computer controlled autoburets, peristaltic pumps, and simultaneous mixing of reagents with or without syringes, may be used to control the mixing of precipitating ions to produce smaller particles.

Due to the small size and nature of calcium/oxyanion particles, they tend to aggregate. Particle aggregation may be inhibited by coating the particles with coating agents. The agglomerated particles may also be disrupted by mechanical or chemical means and then coated with a coating agent having an affinity for the calcium/oxyanion particle. Coating may also be done during synthesis of the particle.

One preferred method of obtaining small, uniformly sized, manganese-doped calcium/oxyanion-containing particles is to dropwise add a degassed solution of $(NH_4)_2HPO_4$ and $NH_4OH$ into a rapidly stirring degassed solution of $Ca(NO_3)_2 \cdot 4H_2O$ and $Mn(NO_3)_2 \cdot 6H_2O$. The resulting apatite particles are then reacted with a solution of a coating agent containing a diphosphonate group. The smaller particles are separated from larger particles by repeated centrifuging and collection of the supernatant. The particles are then washed to remove base and salts by centrifuging at a higher rpm, discarding the supernatant, resuspending the solid pellet in water, and recentrifuging.

The general process to make the coated particles involves mixing together calcium salt, metal salts, salts of oxyanions, salts designed to give electrical neutrality and proper solubility to the resulting solids, an amount of base sufficient to bring the pH of the resultant slurry to above pH=5 and an amount of coating. Before or after the coating is added the slurry may be subjected to mechanical (e.g., microfluidizer) or chemical disruption and, eventually, to desalting procedures to remove excess unwanted salts. The coating can optionally be added to the base solution before mixing with the calcium/metal/oxyanion. A tangential flow filtration (TFF) apparatus can be used to remove excess salts. One or more oxyanion acids (including phosphoric acid) can be used in place of pure phosphoric acid. Aqueous base (including ammonia) can be used for pH adjustment.

Optionally, halogen ion salts or salts of alkali metals or alkaline earth metals can be added to the base or Ca/metal/oxyanion solutions to provide electrical neutrality of and to promote the proper solubility of the resulting particles.

In another method for obtaining small, uniformly sized manganese-doped calcium/oxyanion-containing particles, the particles are prepared by rapidly mixing two solutions, one containing $Mn(NO_3)_2$, $Ca(NO_3)_2$ and $H_3PO_4$ and another containing enough $NH_4OH$ to generate a final pH between about 5 and about 10. The resulting suspension is coated with a diphosphonate or polycarboxylate derivative chemically coupled to a polyalkoxy compound.

Calcium/oxyanion-containing particle precursors include compounds within the scope of the above general formula having one or more amorphous phases. These compounds, when prepared at high temperatures or when sintered, may become crystalline apatites.

Paramagnetic metal ions which can be used in the calcium/oxyanion-containing particles of the present invention include: chromium (III), manganese (II), iron (II), iron (III), praseodymium (III), neodymium (III), samarium (III), ytterbium(III), gadolinium(III), terbium(III), dysprosium(III), holmium(III), erbium(III), or mixtures of these with each other or with alkali or alkaline earth metals.

Certain radiopaque heavy metals, such as bismuth, tungsten, tantalum, hafnium, lanthanum and the lanthanides, barium, molybdenum, niobium, zirconium, and strontium may also be incorporated into particles to provide X-ray contrast. The radiopaque metals are incorporated into the calcium/oxyanion-containing particles in the same manner as paramagnetic metal ions.

Calcium/oxyanion-containing particles include calcium phosphate minerals, apatites, and apatite precursors.

Oxyanions for use with the invention include tetrahedral oxyanions, carbonates, and mixtures thereof.

Typical simple anions which can be used in the calcium/oxyanion-containing particles of the present invention include: $OH^-$, $F^-$, $Br^-$, $I^-$, $1/2[CO_3^{2-}]$, or mixtures thereof. The tetrahedral oxyanions used in the present invention may optionally include radiopaque metals or radioactive metals. Suitable tetrahedral oxyanions are nonoxidizing and stable to hydrolysis. Examples of suitable tetrahedral oxyanions for use in the present invention include: $PO_4^{3-}$, $AsO_4^{3-}$, $WO_4^{2-}$, $MoO_4^{2-}$, $VO_4^{3-}$, $SiO_4^{4-}$, and $GeO_4^{4-}$. Phosphate is a currently preferred tetrahedral oxyanion.

Alkali and alkaline earth metals can be used in the invention. Typically, alkaline earth metals will be used as a substitute for calcium. The alkali metals are believed to aid in charge neutrality (especially when +3 metals are used) and solubility properties.

Alkali and alkaline earth metals include lithium, sodium, potassium, rubidium, cesium, francium, beryllium, magnesium, calcium, strornium, barium and radium.

By controlling average particle size, organ specific imaging or therapy of the liver or gastrointestinal tract is obtained. When apatite particles having an average size in range from about 5 nm to about 5 μm are injected into the vascular system, the particles can collect in the liver or spleen (the reticuloendothelial system known as the RES system). A normal function of the liver and spleen is to purify foreign particles from the blood. Once the particles have collected in the liver or spleen, these organs may be imaged by the desired medical diagnostic imaging technique. For blood pool imaging, particles of the same size or smaller ($\leq 1$ nm) can be used. These particles must reside in the blood pool for long enough to acquire an image. Agents of the invention can also be used for lymphography, tumor selective enhancement, optical imaging, and extracellular contrast enhancement.

Depending on the diagnostic imaging technique, calcium/oxyanion containing particles are treated to be paramagnetic or radiopaque. For example, paramagnetic metal species may be incorporated into the particles to improve magnetic resonance contrast, and radiopaque species may be incorporated to provide X-ray contrast. The calcium/oxyanion-containing particles may also be fluorinated to form stable, nontoxic compositions useful for $^{19}F$ imaging. The presence of a paramagnetic metal species in these particles may reduce $^{19}F$ and proton relaxivity, thereby enhancing MRI, magnetic resonance spectroscopy (MRS), or magnetic resonance spectroscopy imaging (MRSI).

Antioxidants, such as gentisic acid and ascorbic acid, added during or after calcium/oxyanion-containing particle synthesis may be used to prevent metal ion oxidation. Reducing agents, such as $NaBH_4$, have been found to reduce metal ions that are unintentionally oxidized during calcium/oxyanion particle synthesis.

Paramagnetic particles may also be prepared by absorbing paramagnetic metal ions onto the particle. For example, manganese can be adsorbed to calcium/oxyanion particles by taking a slurry of calcium/oxyanion particles and adding $Mn(NO_3)_2$ with stirring. Applying energy, such as ultrasonic power or heat, to the resulting mixture may also facilitate the reaction. The resulting mixture can be separated by either centrifugation and decantation or by filtration. Any excess manganese may be removed by washing with large amounts of water. The manganese adsorbed particles can then be stabilized against oxidation and particle agglomeration with a suitable coating. The same procedure may be used with other paramagnetic cations. The amount of manganese adsorbed onto the particle surface, as a percentage of the total calcium in the particle, is in the range from about 0.1% to about 50%.

The process for making particles of the invention is new. Calcium, maganese and phosphate are in one reaction vessel and the base in another. Rapid mixing is accomplished by passage of both solutions simultaneously through a static mixer. This mixing is controlled so that the two solutions, which are present initially in equal volumes, are mixed at about a 1:1 ratio. Mixing these two solutions in this way results in a rapid, uniform pH change in the Ca, Mn and phosphate solution, since, as each small aliquot of Ca/Mn/phosphate solution enters the static mixer an equal amount of base enters. What comes out the other side are particles made by this "pH jump" method. The slurry generated by passage through the first static mixer could also be mixed with a coating solution by passage of the slurry and coating solution simultaneously through a second mixer. This leads to a shorter time to complete the reaction and workup. A good yield of small particles are generated.

The coating can also be present with the Mn, Ca and phosphate. This allows good mixing and, at the instant the particles are formed, the coating is available to coat the particles, instead of being added later. This leads to removal of one step from the process.

Stabilized calcium/oxyanion-containing particles, including apatites and apatite precursors, are desirable for in vivo use as medical diagnostic imaging agents. Such particles tend to aggregate. Although the reasons calcium/oxyanion-containing particles aggregate is not fully understood, it has been found that several different coatings are able to inhibit particle aggregation. For example, these particles may be stabilized by treatment with coatings such as di- and polyphosphonate-containing compounds or their salts, such as 1-hydroxyethane-1,1-diphosphonate (HEDP), pyrophosphate, aminophosphonates, or any of these moieties attached to a long polymeric chain; carboxylates and polycarboxylate-containing compounds such as oxalates and citrates; alcohols and polyalcohol-containing compounds; compounds containing one or more phosphate, sulfate, or sulfonate moiety; and biomolecules such as peptides, proteins, antibodies, and lipids all of which may or may not have been attached to a long polymeric chain; or combinations of the above. Such coatings can stabilize the small particles by reducing further particle growth, promoting particle suspension, enhancing blood residence tissue, and/or organ and tissue specificity.

Long polymeric chains for use with this invention include polymeric alkoxy derivatives that have been coupled to a group capable of making a tight binding to the surface of the particle. Long polymeric chains derived from poly(ethylene glycol) (PEG), poly(propylene glycol) and co-polymers of propylene and ethylene glycol are examples of the polymeric alkoxy derivatives. The number of ethylenegylcyol and/or propyleneglycol units is between about 2 and about 1000. The polymeric alkoxy derivatives may have one end capped with an alkyl group or suitable protecting group to prevent further reaction at that end and/or to impact desirable chemical reactiveness. Although not required, coupling of the polymeric alkoxy derivative to the binding group can be done through a coupling group of a chain of about 1 to about 10 atoms. The chain can be made up of carbon atoms where some of the carbons may be replaced by N, O, S or P atoms or combinations thereof. Where appropriate, the atoms may contain branching groups such as OH, $CO_2H$, $PO_3H_2$, $SO_3H$, alkyl or substituted alkyl groups, F, Cl, Br, I, $N(R)_2$ (R=alkyl, OH or H). Examples of groups that may be coupled to the polymeric alkoxy derivative include binding groups containing free dior polyphosphonates, polycarboxylates, di- or polyphosphates or mixtures of phosphonates, carboxylates and phosphates. Other groups such as alcohols, thiols or ethers may also be included. The alkyl groups can be substituted with OH, $PO_3H_2$, $SO_3H$, $CO_2H$ and/or polymeric alkoxy groups. The general formula of the coating will be

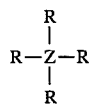

wherein R is present or not, and is the same or different, and is a polymeric alkoxy group, particle binding group, H, OH, a biomolecule, $CO_2H$, $PO_3H_2$, $SO_3H$, alkyl of about 1 to about 5 carbons, substituted alkyl, F, Cl, Br, I, or $N(R^1)_2$ wherein $R^1$ is alkyl, polymeric alkoxy, biomolecule, substituted alkyl, OH or H; Z is present or not, and is a chain made up of about 10 atoms of C, N, O, S, P, or combinations thereof; provided at least one R is a polymeric alkoxy group and at least one R is a particle binding group.

Biomolecule refers to all natural and synthetic molecules that play a role in biological systems. Biomolecules include hormones, amino acids, peptides, peptidomimetics, proteins, deoxyribonucleic acid (DNA) ribonucleic acid (RNA), lipids, albumins, polyclonal antibodies, receptor molecules, receptor binding molecules, monoclonal antibodies and aptamers. Specific examples of biomolecules include insulins, prostaglandins, growth factors, liposomes and nucleic acid probes. Examples of synthetic polymers include polylysine, arborols, dendrimers, and cyclodextrins. The advantages of using biomolecules include enhanced tissue targeting through specificity and delivery. Coupling of the chelating moieties to biomolecules can be accomplished by several known methods (e.g., Krejcarek and Tucker *Biochem, Bioshys. Res. Comm,* 30, 581 (1977); Hnatowich, et al. *Science,* 220, 613 (1983). For example, a reactive moiety present in one of the R groups is coupled with a second reactive group located on the biomolecule. Typically, a nucleophilic group is reacted with an electrophilic group to form a covalent bond between the biomolecule and the chelate. Examples of nucleophilic groups include amines, anilines, alcohols, phenols, thiols and hydrazines. Electrophilic group examples include halides, disulfides, epoxides, maleimides, acid chlorides, anhydrides, mixed anhydrides, activated esters, imidates, isocyanates and isothiocyanates. The above coatings may also be used in combination with simple diphosphonate coatings such as HEDP, MDP or the like.

It is believed polymeric alkoxy derivative coatings render the agents not recognizable by opsonizing agents in the body that would, without the derivatives, direct particles very rapidly toward the liver. The significantly increased blood residence time compared to HEDP-coated particles is believed due to PEGs making these particles look more like "natural" materials thereby going undetected by the normal mechanisms that clear particles from the blood. (See J. of *Liposome Research* 2(3), 289–305 (1992) and Gref et al., *Science* 263:1600 (1994).

When used in magnetic resonance imaging, particle relaxivity is enhanced by allowing more water accessible to the particle surface. By limiting particle size and increasing the available surface area, relaxivity may be improved.

In addition to the coatings identified above, conventional particle coating techniques may also be used in the manufacturing processes of the present invention. Typical coating techniques are identified in International Publication Numbers WO 85/02772, WO 91/02811, and European Publication Number EP 0343934, which are incorporated herein by reference.

It will be appreciated that the calcium/oxyanion-containing particles within the scope of the present invention may be coated before, during, or after passage through a microfluidizer. When coated during passage through the microfluidizer, one fluid stream is the coating agent, while the other fluid stream is the particulate stream and these are mixed immediately before microfluidization takes place.

The currently preferred mechanical means for reducing particle size is microfluidization, but other means such as heating, sonication, other forms of particle energization, such as irradiation, and chemical means, such as pH modification or combinations of these types of treatment, such as pH modification combined with sonication may be used.

The calcium/oxyanion-containing particles of this invention may be formulated into diagnostic compositions for parenteral administration (agents). For example, parenteral formulations advantageously contain a sterile aqueous solution or suspension of treated apatite or apatite precursor particles according to this invention. Various techniques for preparing suitable pharmaceutical solutions and suspensions are known in the art. Such solutions also may contain pharmaceutically acceptable antioxidants, suspension stabilizing polymers, electrolytes such as sodium chloride, or agents to increase the tonicity of the solution. Parenteral compositions may be injected directly or mixed with a large volume parenteral composition for systemic administration. The diagnostic compositions of this invention are used in a conventional manner in medical diagnostic imaging procedures such as magnetic resonance or X-ray imaging. The diagnostic compositions are administered in a sufficient amount to provide adequate visualization, to a warm-blooded animal, either systemically or locally to an organ or tissues to be imaged, then the animal is subjected to the medical diagnostic procedure. Such doses may vary widely, depending upon the diagnostic technique employed as well as the organ to be imaged.

The compositions of the invention can be formulated into diagnostic compositions for enteral or parenteral administration. These compositions contain an effective amount of the agents along with conventional pharmaceutical carriers and excipients appropriate for the type of administration contemplated. For example, for MRI parenteral formulations advantageously contain a sterile aqueous solution or suspension of from about 0.001 to about 1.0M of a paramagnetic ion-containing particle according to this invention. Parenteral compositions may be injected directly or mixed with a large volume parenteral composition for systemic administration. Preferred parenteral formulations have a concentration of paramagnetic ion complex of about 0.001M to about 0.5M. Such solutions also may contain pharmaceutically acceptable antioxidants, buffers, electrolytes such as sodium chloride, or agents to increase the tonicity of the solution.

Formulations for enteral administration may vary widely, as is well-known in the art. In general, such formulations are liquids which include an effective amount of the paramagnetic ion particle in suspension. Such enteral compositions may optionally include buffers, surfactants, thixotropic agents, antioxidants and the like. Compositions for oral administration may also contain flavoring agents and other ingredients for enhancing their organoleptic qualities.

The diagnostic compositions are administered in doses effective to achieve the desired enhancement of the image. For example, in MRI such doses may vary widely, depending upon the particular paramagnetic ion complex employed, the organs or tissues which are the subject of the imaging procedure, the imaging procedure, the imaging equipment being used, and the like. In general, parenteral dosages will range from about 0.001 to about 1.0 mMol of paramagnetic ion complex per kg of patient body weight. Preferred parenteral dosages range from about 0.001 to about 0.5 mMol of paramagnetic ion complex per kg of patient body weight. Enteral dosages generally range from about 0.5 to about 100 mMol, preferably from about 1.0 to about 10 mMol, more preferably from about 1.0 to about 10.0 mMol of paramagnetic ion complex per kg of patient body weight.

The diagnostic compositions of the invention are used in the conventional manner. The compositions may be administered to a patient, typically a warm-blooded animal, either systemically or locally to the organ or tissue to be imaged, and the patient then subjected to the imaging procedure. Protocols for imaging and instrument procedures are found in texts such as Stark, D.D.; Bradley, W.G. *Magnetic Resonance Imaging;* Mosby Year Book: St. Louis, MO, 1992.

X-ray contrast Imaging Procedures are found in Albert A. Moss, M.D., Gordon Gamsu, M.D., and Harry K. Genant, M.D., *Computed Tomography of the Body,* (W.B. Saunders Company, Philadelphia, Pennsylvania 1992) and M. Sovak, Editor, *Radiocontrast Agents,* (Springer-Verlag, Berlin 1984).

The following examples illustrate the specific embodiments of the invention described in this document. As would be apparent to skilled artisans, various changes and modifications are possible and are contemplated within the scope of the invention described.

EXAMPLES

EXAMPLE 1

Preparation of the Bis(tetra-n-butylammonium) salt of 1-amino-3-hydroxypropane-1,1-diphosphonic acid.

1-Amino-3-hydroxypropane-1,1-diphosphonic acid (76.3g, 324 mmol) was mixed with 425.5 mL of an aqueous 40% tetra-n-butyl ammonium hydroxide solution (649 mmol), and the mixture stirred at 60° C. until a clear solution was obtained. The water was then removed by vacuum distillation, and the resulting gummy residue dried in vacuo at 40° C. for 18 hr. The residue was taken up in methylene chloride (750 mL), the cloudy suspension dried over anhydrous sodium sulfate, filtered, and the solvent removed in vacuo to give 226.9 g (97% yield) of the bis(tetra-n-butylammonium) salt of 1-amino-3-hydroxypropane- 1,1-diphosphonic acid.

EXAMPLE 2

Preparation of [methyl(polyoxyethylene)]oxyacetyl chloride

A magnetically-stirred 2-L round-bottomed flask was charged with oxalyl chloride (700 mL, 8.0 mol). The vessel was cooled in an ice-water bath to below 10° C. Methyl(polyoxyethylene)]oxyacetic acid (avg. mol. wt. ca. 2000)(277.7 g, ca. 135 mmol) was added in portions over a 30 min. period, followed by dropwise addition of N,N-dimethylformamide over a 60 min. period, maintaining the temperature below 10° C. The ice-water bath was removed, and the vessel was slowly heated. At ca. 32° C., a vigorous reaction ensued, and the heat source was removed. when the reaction subsides, heating was continued, and the solution was heated at gentle reflux for 15 hr. After cooling to room temperature (20°–25° C.), the oxalyl chloride was removed in vacuo. Dry methylene chloride (200 mL) was added, then removed in vacuo. the methylene chloride treatment was repeated, the residue was taken up again in dry methylene chloride (500 mL), concentrated in vacuo, and heated at 40° C. under vacuum for 16 hr. to obtain 299 g of crude [methyl(polyoxyethylene)]oxyacetyl chloride as a wax.

EXAMPLE 3

Preparation of 1-hydroxy-3-{[methyl(polyoxyethylene)] oxyacetamido}-propane-1,1-diphosphonic acid The bis(tetra-n-butylammonium) salt of 1-amino- 3-hydroxypropane-1,1-diphosphonic acid (138 g,192 mmol) was mixed with toluene (700 mL) and the mixture dried by azeotropic distillation with a Dean-stark trap. After cooling to room temperature, the toluene was removed in vacuo, and the residue dissolved in anhydrous acetonitrile (250 mL). To this was added a solution of the crude [methyl(polyoxyethylene)]oxyacetyl chloride (299 g) in anhydrous acetonitrile (250 mL), followed by dry triethylamine (138 mL, 100 g, 990 mmol). The solution was heated and stirred at 70° C. for 4 days, after which time the solvent was removed in Vacuo. The residue was dissolved in water (600 mL) and eluted through 500 mL of Amberlite IR-120 resin (H+form). The brown eluent was collected, the water removed in vacuo, and the waxy residue redissolved in water (800 mL). The product solution was loaded onto a column containing 3.5 L of Amberlite IRA-68 resin, and eluted with 0.25M acetic acid, followed by 10 L of 0.5M acetic acid, collecting 2-L fractions. Portions of each fraction were concentrated and analyzed by $^1$H and $^{31}$p-NMR. Fractions containing product ($^{31}$P resonance at ca 19 ppm downfield from 85% $H_3PO_4$) were combined, concentrated in vacuo, and re-chromatographed on 1 L of fresh IRA-68 resin, eluting with a sodium acetate gradient (0–25 mM). The purest fractions were combined, eluted through Amberlite IR-120 resin ($H^+$form) to remove sodium ions, the solvent removed in vacuo, and the product dried in vacuo to give 18 g of 1-hydroxy-3-{[methyl(polyoxyethylene)]oxyacetamido}-propane-1-1-diphosphonic acid as a waxy solid.

EXAMPLE 4

Synthesis of 15% MnHA//20% diphosphonate for blood pool

METALS AND PHOSPHATE: A metal ion solution was prepared by mixing 0.26 g of Mn(NO3)2.4.5H2O, or 1 mmole; 1.33 g of $Ca(NO_3)_2.4H_2O$, or 5.66 mmole; 0.46 g of $NH_4H_2PO_4$, or 4 mmole; and 0.2 ml of 1M $H_3PO_4^3$ together with water to a final volume of 20 ml. This solution was deaerated prior to use.

BASE: Aqueous ammonia (11 ml. 1M) was diluted to 20 ml for use.

STABILIZING AGENT: 4.0 g of PEG(2000-APD) was dissolved in 20 ml of water and the pH was adjusted to 9 with 1M aqueous ammonia.

PARTICLES: The metal and base were simultaneously passed through a static mixer at room temperature, causing rapid mixing, and stirred for 30 minutes The pH at this state is ~8.

The stabilizing agent was then added at room temperature and stirred for an extra 1 hr. The slurry was microfluidized while being cooled to 4° C. at 15,000 psi to break up aggregates and the product was purified of small ions and unbound stabilizing agent by tangential flow filtration at room temperature until the conductivity of the effluent dropped to ~200 uS (this typically required ~12 volume-equivalents of effluent).

PRODUCT: Approximately 70 ml of product is obtained with [Mn] of ~10 mM, diameter <50 nm, R1 between 16–20 $mM^{-1}$ $sec^{-1}$ $^{1, and\ R}2$ between 20–24 $mM^{-1}$ $sec^{-1}$.

EXAMPLE 5

Preparation of [methyl(polyoxyethylene)]oxyacetyl chloride

A magnetically-stirred 1-L round-bottomed flask fitted with a Dean-Stark trap and a reflux condenser was charged with methyl(polyoxyethylene)]oxyacetic acid (avg. mol. wt. ca. 2000) (135 g, ca. 65 mmol) and toluene (500 mL). The resulting solution was dried azeotropically by heating at reflux and collecting the distillate in a Dean-Stark trap until the distillate was clear and water no longer separated out (ca. 2 hours). The toluene was removed in vacuo, and oxalyl chloride was added. The reaction vessel was fitted with a reflux condenser connected to a gas bubbler, and the resulting solution was heated at reflux until gas evolution ceased, allowed to cool to room temp. (20°–25° C.), and the excess oxalyl chloride removed in vacuo to give the acid chloride as a waxy solid.

EXAMPLE 6

Preparation of 1-hydroxy-3-{[methyl(polyoxyethylene)] oxyacetamido}-propane-1,1-diphosphonic acid

[Methyl(polyoxyethylene)]oxyacetyl chloride (prepared above) was dissolved in toluene (300 mL) and added dropwise, over 2 hours, to a vigorously stirred solution of 3-amino-1-hydroxypropane-1,1-diphosphonic acid (15 g, 64 mmol) in 1N aqueous sodium hydroxide (330 mL, 330 mmol). The reaction mixture was stirred at room temp. for 18 hours, the toluene removed in vacuo, and the resulting aqueous solution eluted through 330 mL of Amberlite IR-120 cation exchange resin (H+form), followed by 500 mL of water. The total eluent was evaporated to dryness in vacuo, then redissolved in water (1 L) and purified by preparative HPLC on 450 g of SynChrom Synchroprep AX-300 resin in a stainless steel column. After applying the product mixture to the column, the column was eluted (at a flow rate of 50 mL/min) with water (2 L), followed by a step gradient of aqueous sodium acetate (20 mM per step, 500 mL between steps), collecting 500 mL fractions. The fractions containing pure product were combined, concentrated, eluted through Amberlite IR-120 cation exchange resin (H+form) to remove sodium, and evaporated to dryness. The resultant waxy solid was redissolved in water, titrated with 1N aqueous NaOH to pH 7.1, evaporated to a gummy solid, redissolved in absolute ethanol, and evaporated to a solid to give 40 g of 1-hydroxy-3-{[methyl(polyoxyethylene)]oxyacetamido)-propane-1,1-diphosphonic acid as its trisodium salt.

EXAMPLE 7

Synthesis of 15% MnHA/40% diphosphonate for blood pool

METALS AND PHOSPHATE: A metal ion solution was prepared by mixing 0.26 g of $Mn(NO_3)_2.4.5H_2O$, or 1 mole; 1.33 g of $Ca(NO_3)_2.4H_2O$, or 5.66 mmole; 0.46 g of $NH_4H_2PO_4$, or 4 mmole; and 0.2 ml of 1M $H_3PO_4$ together with water to a final volume of 20 ml. This solution was deaerated prior to use. BASE: Aqueous ammonia (11 ml, 1M) was diluted to 20 ml to use.

STABILIZING AGENT: 8.0 g of PEG(2000)-APD (i.e., methoxypolyethyleneglycol-2000 with one terminal 3-aminopropane-1,1-diphosphonic acid) was dissolved in 20 ml of water and the pH was adjusted to 9 with 1M aqueous ammonia.

PARTICLES: The metal and base were simultaneously passed through a static mixer at room temperature causing rapid mixing and stirred for 30 minutes. The pH at this state was about 8.

The stabilizing agent was then added at room temperature, and the mixture was stirred for an extra 1 hour. The product was purified of small ions and unbound stabilizing agent by tangential flow filtration at room temperature until the conductivity of the effluent dropped to about 200 uS (this typically required about 12 volume-equivalents of effluent).

PRODUCT: Approximately 70 ml of product is obtained with [Mn] of about 10 mM, diameter less than 50 nm, R1 between 16–20 $mM^{-1}$ $sec^{-1}$, and R2 between 20–24 $mM^{-1}$ $sec^{-1}$.

EXAMPLE 8

Synthesis of 15% MnHA//20% diphosphonate for blood pool where diphosphonate added at beginning of the reaction METALS, PHOSPHATE AND COATING AGENT: A metal ion solution was prepared by mixing 0.26 g of $Mn(NO_3)_2.5H_2O$, or 1 mmole; 1.33 g of $Ca(NO_3)_2.4H_2O$, or 4.66 mmole; 0.46 g of $NH_4H_2PO_4$, or 4 mmole; and 0.2 ml of 1M $H_3PO_4$ together with 8.0 g of PEG(2000)-APD (i.e., methoxypolyethleneglycol-2000 with one terminal 3-aminopropane-1,1-diphosphonic acid group) and enough water to make a final volume of 20 ml. This solution was deaerated prior to use.

BASE: Aqueous ammonia (ca 12 ml. 1M) was diluted to 20 ml for use.

PARTICLES: The metal/phosphate/coating agent solution and the base solution were mixed rapidly and stirred for 30 minutes. The pH at this state is about 8. The resulting solution was microfluidized at 15,000 psi to break up aggregates and the product was purified of small ions and unbound stabilizing agent by tangential flow filtration until the conductivity of the effluent dropped to about 200 uS (this typically required about 12 volume-equalivants of effluent).

PRODUCT: Approximately 70 ml of product is obtained with [Mn] of about 10 mM, yield about 70% base on startint Mn. The diameter <50 nm from photon correlation spectroscopy on the Nicomp. Relaxivities were; -R1 between 16–20 $mM^{-1}$ $sec^{-1}$, and R2 between 20–24 $mM^{-1}$ $sec^{-1}$.

Although the invention has been described with respect to specific modifications, the details thereof are not to be construed as limitations, for it will be apparent that various equivalents, changes and modifications may be resorted to without departing from the spirit and scope thereof, and it is understood that such equivalent embodiments are to be included therein.

What is claimed is:

1. A diagnostic agent comprising a compound of the general formula:

$$Ca_nM_mX_sY_s$$

wherein M is a paramagnetic ion or stoichiometric mixture of metal ions having a valence of 2+ or 3+; X is a simple anion; Y is a tetrahedral oxyanion, or mixtures thereof; m is $\geq 1$; n is $\geq 1$; r and s are integers and adjusted as needed to provide charge neutrality; and further comprising a coating comprising a polymeric alkoxy compound.

2. The diagnostic agent of claim 1 wherein the polymeric alkoxy compound is of the general formula:

$$\begin{array}{c} R \\ | \\ R-Z-R \\ | \\ R \end{array}$$

wherein R is present or not, and is the same or different, and is a polymeric alkoxy group, particle binding group, H, OH, a biomolecule, $CO_2H$, $PO_3H_2$, $SO_3H$, alkyl of about 1 to about 5 carbons, substituted alkyl, F, Cl, Br, I, or $N(R^1)_2$ wherein $R^1$ is alkyl, polymeric alkoxy, biomolecule, substituted alkyl, OH or H; Z is a bond or is a chain made up of about 1 to about 10 atoms of C, N, O, S, P, or combinations thereof; provided at least one R is a polymeric alkoxy group and at least one R is a particle binding group.

3. The diagnostic agent of claim 2 wherein the polymeric alkoxy compound is comprised of ethylene glycol and/or propylene glycol units with the total number of units being between about 2 and about 1000.

4. The diagnostic agent of claim 3 wherein the polymeric alkoxy derivative is poly(ethylene glycol).

5. The diagnostic agent of claim 4 wherein the poly(ethylene glycol) comprises between about 2 and about 200 units of ethylene glycol.

6. The diagnostic agent of claim 4, in which the paramagnetic metal is chromium (III), manganese (II), iron (II), iron (III), praseodymium (III), neodymium (III), samarium (III), ytterbium (III), gadolinium (III), terbium (III), dysprosium (III), holmium (III), erbium (III), or mixtures thereof, with or without alkali or alkaline earth metals.

7. The diagnostic agent of claim 4 wherein X is $OH^-$, $F^-$, $Br^-$ $I^-$, $1/2[CO_3^{2-}]$, or mixtures thereof.

8. The diagnostic agent of claim 4 wherein Y is phosphate, arsenate, tungstate, molybdate, vanadate, silicate, germanate, or mixtures thereof.

9. The diagnostic agent of claim 6 wherein Y is phosphate, X is $OH^-$ or r is zero, and M is Mn.

10. The diagnostic agent of claim 9 wherein the percent of Mn to total metal is between about 5 and about 25 percent.

11. The diagnostic agent of claim 1 wherein the polymeric alkoxy compound has an average molecular weight of about 1500 to about 5500.

12. The diagnostic agent of claim 11 wherein the coating agent is 1-hydroxy-3-{[methyl(polyoxyethylene)]oxyacetamido}-propane-1,1-diphosphonic acid of average molecule weight of about 2100.

13. The diagnostic agent of claim 12 wherein the average particle size is greater than or equal to about 1 nm but less than about 5 μm.

14. A diagnostic agent comprising a compound of the general formula:

$$Ca_nM_mX_rY_s$$

wherein M is a radiopaque heavy metal; X is a simple anion; Y is a tetrahedral oxyanion, or mixtures thereof; m is $\geq 1$; n is $\geq 1$; r and s integers and adjusted as needed to provide charge neutrality; and further comprising a coating comprising a polymeric alkoxy compound.

15. The diagnostic agent of claim 14 wherein the polymeric alkoxy compound is of the general formula:

$$\begin{array}{c} R \\ | \\ R-Z-R \\ | \\ R \end{array}$$

wherein R is present or not, and is the same or different, and is a polymeric alkoxy group, particle binding group, H, OH, a biomolecule, $CO_2H$, $PO_3H_2$, $SO_3H$, alkyl of about 1 to about 5 carbons, substituted alkyl, F, Cl, Br, I, or $N(R^1)_2$ wherein $R^1$ is alkyl, polymeric alkoxy, biomolecule, substituted alkyl, OH or H; Z is present or not, and is a chain made up of about 10 atoms of C, N, O, S, P, or combinations thereof; provided at least one R is a polymeric alkoxy group and at least one R is a particle binding group.

16. The diagnostic agent of claim 15 wherein the polymeric alkoxy compound is comprised of ethylene glycol and/or propylene glycol units with the total number of units being between about 2 and about 1000.

17. The diagnostic agent of claim 16 wherein the polymeric alkoxy derivative is poly(ethylene glycol).

18. The diagnostic agent of claim 17 wherein the poly(ethylene glycol) comprises between about 2 and about 200 units of ethylene glycol.

19. The diagnostic agent of claim 17, in which the radiopaque heavy metal is bismuth, tungsten, tantalum, hafnium, lanthanum, barium, molybdenum, niobium, zirconium, or strontium.

20. The diagnostic agent of claim 17 wherein X is $OH^-$, $F^-$, $Br^-$, $I^-$, $1/2[CO_3^{2-}]$, or mixtures thereof.

21. The diagnostic agent of claim 17 wherein Y is phosphate, arsenate, tungstate, molybdate, vanadate, silicate, germanate, or mixtures thereof.

22. The diagnostic agent of claim 21 wherein Y is phosphate, X is $OH^-$ or r is zero, and M is bismuth.

23. The diagnostic agent of claim 22 wherein the percent of Mn to total metal is between about 5 and about 25 percent.

24. The diagnostic agent of claim 23 wherein the polymeric alkoxy compound has an average molecular weight of about 1500 to about 5500.

25. The diagnostic agent of claim 24 wherein the polymeric alkoxy compound is 1-hydroxy-3-{[methyl(polyoxyethylene)]oxyacetamido}-propane-1,1-diphosphonic acid of average molecule weight of about 2100.

26. The diagnostic agent of claim 25 wherein the average particle size is greater than or equal to about 1 nm but less than about 5 μm.

27. A method of imaging comprising administering to a patient a compound of the general formula:

$$Ca_nM_mX_rY_s$$

wherein M is a paramagnetic ion or stoichiometric mixture of metal ions having a valence of 2+ or 3+; X is a simple anion; Y is a tetrahedral oxyanion, or mixtures thereof; m is $\geq 1$; n is $\geq 1$; r and s are integers and adjusted as needed to provide charge neutrality; and further comprising a coating comprising a polymeric alkoxy compound.

28. The method of claim 27 wherein the polymeric alkoxy compound is of the general formula:

$$\begin{array}{c} R \\ | \\ R-Z-R \\ | \\ R \end{array}$$

wherein R is present or not, and is the same or different, and is a polymeric alkoxy group, particle binding group, H, OH, a biomolecule, $CO_2H$, $PO_3H_2$, $SO_3H$, alkyl of about 1 to about 5 carbons, substituted alkyl, F, Cl, Br, I, or $N(R^1)_2$ wherein $R^1$ is alkyl, polymeric alkoxy, biomolecule, substituted alkyl, OH or H; Z is a bond or is a chain made up of about 1 to about 10 atoms of C, N, O, S, P, or combinations thereof; provided at least one R is a polymeric alkoxy group and at least one R is a particle binding group.

29. The method of claim 28 wherein the polymeric alkoxy compound is comprised of ethylene glycol and/or propylene glycol units with the total number of units being between about 2 and about 1000.

30. The method of claim 29 wherein the polymeric alkoxy derivative is poly(ethylene glycol).

31. The method of claim 30 wherein the poly(ethylene glycol) comprises between about 2 and about 200 units of ethylene glycol.

32. The method of claim 30, in which the paramagnetic metal is chromium (III), manganese )II), iron (II), iron (III), praseodymium (III), neodymium (III), samarium (III), ytterbium (III), gadolinium (III), terbium (III), dysprosium (III), holmium (III), erbium (III), or mixtures thereof, with or without alkali or alkaline earth metals.

33. The method of claim 30 wherein X is $OH^-$, $F^-$, $Br^-$, $I^-$, $1/2[CO_3^{2-}]$, or mixtures thereof.

34. The method of claim 30 wherein Y is phosphate, arsenate, tungstate, molybdate, vanadate, silicate, germanate, or mixtures thereof.

35. The method of claim 32 wherein Y is phosphate, X is $OH^-$ or r is zero, and M is Mn.

36. The method of claim 35 wherein the percent of Fin to total metal is between about 5 and about 25 percent.

37. The method of claim 28 wherein the polymeric alkoxy compound has an average molecular weight of about 2000 to about 5000.

38. The diagnostic agent of claim 11 where the coating agent is 1-hydroxy-3-{[methyl(polyoxyethylene)]xyacetamido}-propane-1,1-diphosphonic acid of average molecule weight of about 2100.

39. The method of claim 38 wherein the average particle size is greater than or equal to about 1 nm but less than about 5 μm.

40. A method of imaging comprising administering to a patient a compound of the general formula:

$$Ca_nM_mX_rY_s$$

wherein M is a radiopaque heavy metal; X is a simple anion; Y is a tetrahedral oxyanion, or mixtures thereof; m is $\geq 1$; n is $\geq 1$; r and s integers and adjusted as needed to provide charge neutrality; and further comprising a coating comprising a polymeric alkoxy compound.

41. The method of claim 40 wherein the polymeric alkoxy compound is of the general formula:

$$\begin{array}{c} R \\ | \\ R-Z-R \\ | \\ R \end{array}$$

wherein R is present or not, and is the same or different, and is a polymeric alkoxy group, particle binding group, H, OH, a biomolecule, $CO_2H$, $PO_3H_2$, $SO_3H$, alkyl of about 1 to about 5 carbons, substituted alkyl, F, Cl, Br, I, or $N(R^1)_2$ wherein $R^1$ is alkyl, polymeric alkoxy, biomolecule, substituted alkyl, OH or H; Z is a bond or is a chain made up of about 1 to about 10 atoms of C, N, O, S, P, or combinations thereof; provided at least one R is a polymeric alkoxy group and at least one R is a particle binding group.

42. The method of claim 41 wherein the polymeric alkoxy compound is comprised of ethylene glycol and/or propylene glycol units with the total number of units being between about 2 and about 1000.

43. The method of claim 42 wherein the polymeric alkoxy derivative is poly (ethylene glycol).

44. The method of claim 43 wherein the poly(ethylene glycol) comprises between about 2 and about 200 units of ethylene glycol.

45. The method of claim 42, in which the radiopaque heavy metal is bismuth, tungsten, tantalum, hafnium, lanthanum, barium, molybdenum, niobium, zirconium, or strontium.

46. The method of claim 42 wherein X is $OH^-$, $F^-$, $Br^-$, $I^-$, $1/2[CO_3^{2-}]$, or mixtures thereof.

47. The method of claim 42 wherein Y is phosphate, arsenate, tungstate, molybdate, vanadate, silicate, germanate, or mixtures thereof.

48. The method of claim 47 wherein Y is phosphate, X is $OH^-$ or r is zero, and M is bismuth.

49. The method of claim 48 wherein the percent of bismuth to total metal is between about 5 and about 25 percent.

50. The method of claim 49 wherein the polymeric alkoxy compound has an average molecular weight of about 2000 to about 5000.

51. The method of claim 50 wherein the polymeric alkoxy compound is 1-hydroxy-3-{[methyl(polyoxyethylene)]oxyacetamido}-propane-1,1-diphosphonic acid of average molecular weight of about 2100.

52. The method of claim 51 wherein the average particle size is greater than or equal to about 1 nm but less than about 5 μm.

* * * * *